(12) United States Patent
Ito et al.

(10) Patent No.: US 7,932,329 B2
(45) Date of Patent: Apr. 26, 2011

(54) USE OF ALKALI METAL-SILICA GEL (M-SG) MATERIALS IN SOLVENT AND MONOMER DRYING AND PURIFICATION FOR THEIR USE IN ANIONIC POLYMERIZATION

(75) Inventors: Mana Ito, Pessac (FR); Stephane Carlotti, Pessac (FR); Alain Deffieux, Bordeaux (FR); Michael Lefenfeld, New York, NY (US)

(73) Assignees: Signa Chemistry, Inc., New York, NY (US); Laboratoire de Chimie des Polymeres Organiques (FR)

( * ) Notice: Subject to any disclaimer, the term of this patent is extended or adjusted under 35 U.S.C. 154(b) by 0 days.

(21) Appl. No.: 12/239,296

(22) Filed: Sep. 26, 2008

(65) Prior Publication Data

US 2009/0105430 A1 Apr. 23, 2009

Related U.S. Application Data

(60) Provisional application No. 60/976,008, filed on Sep. 28, 2007.

(51) Int. Cl.
*C08F 2/00* (2006.01)
*B01D 15/00* (2006.01)
*C07C 7/12* (2006.01)
*C08F 4/48* (2006.01)

(52) U.S. Cl. ........... 526/77; 526/912; 210/679; 585/820

(58) Field of Classification Search ............ 526/77, 526/912; 210/679; 585/820
See application file for complete search history.

(56) References Cited

U.S. PATENT DOCUMENTS

| 3,149,099 A * | 9/1964 | Groene et al. ............. 526/177 |
| 3,594,982 A | 7/1971 | Pearson |
| 4,087,477 A | 5/1978 | Tazuma et al. |
| 4,835,338 A | 5/1989 | Liu |
| 7,211,539 B2 | 5/2007 | Lefenfeld |
| 7,259,128 B2 | 8/2007 | Lefenfeld |
| 2005/0151278 A1 | 7/2005 | Lefenfeld et al. |
| 2006/0073968 A1* | 4/2006 | Lefenfeld et al. ........... 502/344 |

FOREIGN PATENT DOCUMENTS

EP 0683 147 A 11/1995

OTHER PUBLICATIONS

International Search Report mailed May 15, 2009.

* cited by examiner

*Primary Examiner* — Fred M Teskin
(74) *Attorney, Agent, or Firm* — J.A. Lindeman & Co., PLLC

(57) ABSTRACT

Stage I Group 1 metal/porous metal oxide compositions or Stage II Group 1 metal/porous metal oxide compositions are shown to be useful to remove impurities and act as drying agents for various types of solvents and for olefinic monomers used in anionic polymerizations. One important advantage of these compositions is their ability to dry simultaneously solvent and monomers, without inducing a significant polymerization of the latter. Another important characteristic is the capacity of the compositions to be totally inactive toward conventional anionic polymerization which allows them to be left in situ during the polymerization itself.

23 Claims, No Drawings

US 7,932,329 B2

USE OF ALKALI METAL-SILICA GEL (M-SG) MATERIALS IN SOLVENT AND MONOMER DRYING AND PURIFICATION FOR THEIR USE IN ANIONIC POLYMERIZATION

CROSS REFERENCE TO RELATED APPLICATIONS

This application claims priority under 35 U.S.C. §119 to U.S. provisional application Ser. No. 60/976,008 filed Sep. 28, 2007, which is incorporated herein by reference.

FIELD OF INVENTION

This invention relates to the use of Group 1 metal/porous oxide compositions in the drying and removing of impurities of both solvents and monomers for the use in anionic polymerization. The Group 1 metal/porous oxide compositions used in this invention are easily handled, free-flowing powders, which avoid the need for neat alkali metal or organolithium reagent handling or special equipment to perform tedious vacuum distillations.

BACKGROUND OF INVENTION

Anionic polymerization of olefins is a well-known process and is used in a variety of industries. Solvents and monomers used in the anionic polymerization of ethylenic and vinylic monomers (typically styrenic and dienic monomers) should be thoroughly dried to avoid any deactivation of the propagating active centers before the end of the polymerization reaction. The drying process requires highly efficient agents since the concentration of active species is very low and any residual amount of impurities is sufficient to significantly perturb the polymerization and the control of polymer molar masses and chain functionalization. For example, to achieve the polymerization of polystyrene with an expected and controlled molar mass in the range 10,000 to 100,000 g/mol, and working at monomer concentration of 1 mol/l, the initiator concentration should be in the range $10^{-2}$ to $10^{-3}$ mol/l. This means that a concentration in impurities less than 10% of the active species concentration should be present to get acceptable results. Efficient drying agents should also be able to remove trace impurities in the solvent and in the monomer. Generally, the drying conditions applied to the solvent and to the monomers must be different to avoid any risk of unwanted polymerization of monomers.

Typical drying agents used for solvents at laboratory scale are butyllithium, polystyryllithium, diphenylhexyllithium, activated sodium or potassium (mirrors or metal wires), and sodium-potassium alloys. Some others, of limited number, can be used both for the solvent and monomer such as dialkylmagnesium, aluminum trialkyls, and calcium hydride (although of limited efficiency). Drying at the industrial scale may also be achieved by passing the solvent and monomer over molecular sieves or over activated alumina.

In most cases the solvents and monomers must be subsequently distilled to remove any traces of drying agent, which may affect the polymerization reaction. After this last operation, the solvents and/or monomers are typically transferred into the polymerization reactor under inert atmosphere and are ready for use. These drying processes are tedious and constitute a strong limitation for the development of anionic polymerization both at laboratory and industrial scales. There is, therefore, a need in the art for effective drying agents and impurity removal for anionic polymerization processes. This invention answers that need.

SUMMARY OF THE INVENTION

This invention relates to the use of Group 1 metal/porous oxide compositions for the use of drying and removing impurities in solvents and monomer solutions for their use in anionic polymerization applications. These processes may be performed either in conventional stirred reactors or in continuous flow reactors, where the process may or may not require specialized equipment for alkali metal handling or distillation.

More particularly the invention provides a method for removing impurities from solvents and monomers used in anionic polymerization. In the method a solvent, a liquid monomer, or a solvent-monomer mixture is contacted with a Stage I Group 1 metal/porous metal oxide composition or a Stage II Group 1 metal/porous metal oxide composition.

The invention provides an anionic polymerization process. The steps of this method include the steps of:

contacting a solvent, a liquid monomer, or a solvent-monomer mixture with a Stage I Group 1 metal/porous metal oxide composition or a Stage II Group 1 metal/porous metal oxide composition;

optionally combining the liquid monomer and solvent, when the solvent or the monomer is separately contacted with the Stage I Group 1 metal/porous metal oxide composition or a Stage II Group 1 metal/porous metal oxide composition; and polymerizing the monomer under anionic polymerization conditions.

DETAILED DESCRIPTION OF THE INVENTION

As described above, the invention relates to a method for removing impurities from solvents and monomer solutions used in anionic polymerization. The method contacts a solvent, a liquid monomer, or a solvent-monomer mixture with a Stage I alkali metal/porous metal oxide composition or a Stage II Group 1 metal/porous metal oxide composition. To dry the solvent, liquid monomer, or solvent-monomer mixture thereof, then, means removing water and other protic compounds such as alcohol, as impurities. Methods of the invention may, before or after the contacting step, include the step of distilling the solvent or the liquid monomer.

The invention also provides an anionic polymerization process. The steps of this method include the steps of:

contacting a solvent, a liquid monomer, or a solvent-monomer mixture with a Stage I Group 1 metal/porous metal oxide composition or a Stage II Group 1 metal/porous metal oxide composition;

optionally combining the liquid monomer and solvent, when the solvent or the monomer is separately contacted with the Stage I Group 1 metal/porous metal oxide composition or a Stage II Group 1 metal/porous metal oxide composition; and polymerizing the monomer under anionic polymerization conditions.

The direct addition of monomer alone to a Stage I Group 1 metal/porous metal oxide composition or a Stage II Group 1 metal/porous metal oxide composition may lead to poor results due to any heat generation being caused leading to polymerization of styrene. For that reason it is preferable to add the Stage I Group 1 metal/porous metal oxide composition or a Stage II Group 1 metal/porous metal oxide composition to a solvent-monomer mixture or to add the a Stage I Group 1 metal/porous metal oxide composition or a Stage II Group 1 metal/porous metal oxide composition first to the solvent, followed by addition of the monomer. This may vary depending on the monomer used. The order of addition may also be impact the polymer characteristics.

Stage I Group 1 metal/porous metal oxide compositions and Stage II Group 1 metal/porous oxide compositions (available from SiGNa Chemistry, Inc., New York City, N.Y., Alfa Aesar, Ward Hill, Mass., and Sigma-Aldrich, Milwaukee, Wis.) are very useful in the methods of the invention both for removing impurities (e.g. water, other protic impurities (such as alcohols), peroxides, ethers, etc.) from common organic solvents and from monomers used in anionic polymerizations as well as removing stabilizers and/or inhibitors added to the solvents or monomers. The solvents include, but are not limited to, hydrocarbons such as hexane, heptane, octane, pentane, cyclohexane, or methylcyclohexane; aromatics such as benzene, toluene, xylenes, or pyridine; and ethers such as tetrahydrofuran (THF), methyl-THF, diethyl ether, di-isopropyl ether, 1,4-dioxane, 1,3-dioxane, dimethoxyethane. Exemplary monomers include, but are not limited to, olefinic monomers such as styrene, α-methyl styrene, ring-substituted styrene, 1,3-butadiene, isoprene, 1,3-cyclohexadiene, other conjugated dienes, methyl methacrylate, and other methacrylate monomers. Stage II Group 1 alkali metal/porous oxide materials are also able to remove impurities from solvents that have reducible groups (e.g. Dimethyl formamide, Dimethylsulfoxide, acetone, methyl ethyl ketone, N-methyl pyrrolidine, Acetonitrile, Ethyl acetate, Isopropyl acetate, butyl acetate, Ionic liquids, methyl isobutyl ketone, methylene chloride, chloroform, carbon tetrachloride, all fluorinated solvents, etc.).

The amount of a Stage I Group 1 metal/porous metal oxide composition and Stage II Group 1 metal/porous oxide composition used in the methods of the invention may vary according to the amount and type of impurities to be removed from the particular solvent or monomer. As would be expected, the amount of the Stage I Group 1 metal/porous metal oxide composition or the Stage II Group 1 metal/porous oxide composition used should be at least based on the stoichiometry of one mole of the Group 1 metal (e.g., Na, K, or NaK alloy) per mole of reactive group(s) within the impurity. That is, if water, $H_2O$, is the impurity to be removed, two molar equivalents of a Stage I Group 1 metal/porous metal oxide composition or a Stage II Group 1 metal/porous oxide composition would be used. For monohydric alcohols, such as methanol or ethanol, one molar equivalent may be used. It is preferred however, that at least 20 to 50 percent molar excess be used to ensure complete removal of unwanted impurities. Because, as discussed below, the Stage I Group 1 metal/porous metal oxide compositions and Stage II Group 1 metal/porous oxide compositions do not impede the anionic polymerization when used in situ using excess material is acceptable. In other embodiments of the invention, the solvent or monomer is distilled away from the Stage I Group 1 metal/porous metal oxide composition and Stage II Group 1 metal/porous oxide composition prior to polymerization such that the use of excess material should not impact the polymerization. Another embodiment of the invention uses a column packed with a Stage I Group 1 metal/porous metal oxide composition or a Stage II Group 1 metal/porous oxide composition to remove impurities from the solvent or monomer passed through the column. In the column purification embodiment, the Stage I Group 1 metal/porous metal oxide composition and Stage II Group 1 metal/porous oxide composition is in excess.

Stage I Group 1 Metal/Porous Oxide or Stage II Group 1 Metal/Porous Oxide Compositions Recently, new Group 1 metal/porous oxide compositions having improved handling and safety characteristics have been described. These new materials have an alkali metal or alkali metal alloy absorbed into porous oxides, such as silica gel and alumina gel. The new materials retain the reactivity of the native metal, while being much less dangerous than the bulk metal. Accordingly, the term "Group 1 metal/porous oxide compositions" as used herein refers to the material that is formed when an alkali metal, or an alkali metal alloy, is absorbed into porous oxide compositions. The Stage I Group 1 metal/porous oxide or Stage II Group 1 metal/porous oxide compositions used in the invention may be prepared as disclosed in U.S. Pat. No. 7,211,539 B2 and in U.S. Pat. No. 7,259,128, both of which are hereby incorporated by reference in their entirety.

As is disclosed in U.S. Pat. No. 7,211,539 B2 and U.S. Pat. No. 7,259,128, given the pyrophoric nature of alkali metals and their alloys, the ability to utilize alkali metals or their equivalents in a convenient form continues to be a need in the chemical industry. However, the stability of alkali metals and alkali metal alloys in air can be dramatically improved by absorbing the alkali metals into porous oxide supports. For example, these metals can be made significantly more stable by absorption into silica gel to form the alkali metal-silica gel materials or into porous alumina powders to form alkali metal-alumina materials.

The use of Stage I Group 1 metal/porous metal oxide compositions and Stage II alkali metal/porous oxide materials as drying agents strongly simplifies the necessary procedures to achieve controlled anionic polymerization. Different drying approaches and methods according to the invention are illustrated below by examples of polymerization performed using conventional drying agents and procedures based on the use of Stage I Group 1 metal/porous metal oxide compositions and Stage II alkali metal/porous oxide materials. The main parameters used to check the drying efficiency are 1) the quantitative conversion of monomer into polymer in presence of butyl lithium as initiator and 2) the good agreement between theoretical and experimental polymer molar masses. Complete deactivation of propagating species before total monomer consumption will result in incomplete polymer yield, while partial deactivation will result in polymers with higher molar masses than predicted. These polymerization data give direct information on the presence and the amount of impurities still remaining in the total system after treatment with the alkali metal/porous oxide material or treatment with conventional techniques for purification.

The preferred Stage I Group 1 metal/porous metal oxide compositions and Stage II alkali metal/porous oxide materials include 35-40 wt. % alkali metal or alkali metal alloy in silica gel or alumina gel. For the Stage II compositions, Na, K, NaK, $Na_2K$, $K_2Na$ and $K_5Na$ are the preferred metals. Particularly preferred material include Stage I Group 1 metal-Silica Gel material having 40 wt. % Na loading, Na-SG-I; Stage I $Na_2K$-Silica Gel material having 40 wt. % $Na_2K$ loading, Na$_2$K-SG-I; and the corresponding Stage II Na-Silica Gel material, Na-SG-II.

Purification and Drying of Solvents with Polymerization Efficiency Measurements

To demonstrate the removal of water and other impurities, several exemplary solvents typically used in anionic polymerizations were contacted with Na-SG-I according to the invention. Suitable solvents include linear hydrocarbons such as heptane, cyclohexane, methylcyclohexane, benzene, toluene, ethylbenzene and other substituted benzene derivatives, tetrahydrofuran and other ether solvents. In the following procedures, a comparison is made between conventional (Method A) and alkali metal/porous oxide material based (Method B) drying procedures. The efficacy of each method was measured by performing standard anionic polymerization tests using an alkyllithium initiator. All polymerization reactions were carried out at room temperature under vacuum conditions in glassware previously flamed under vacuum, equipped with a magnetic stirrer and PTFE stopcocks.

EXAMPLE 1

Effect of Different Techniques Used as Drying Agents for the Cyclohexane Used as the Polymerization Solvent Method A. Cyclohexane (50 ml) was poured into a 100 ml glass flask equipped with PTFE stopcocks. Continuously, styrene (0.3 ml) and sec-butyllithium (~0.5 ml of 1.4 M solution in cyclohexane) are added to the solvent. After a few minutes, the appearance of a bright orange color indicates the formation of polystyryllithium, meaning that the solvent is dry. Prior use, the solvent is distilled from the polystyryllithium solution under vacuum conditions and transferred into the polymerization vessel.

Method B. Na-SG-I (100 mg) was introduced into a 100 ml glass flask equipped with PTFE stopcocks. This manipulation was carried out in a glove box. Then, cyclohexane (50 ml) was poured into the flask under inert atmosphere and stirred with Na-SG-I for 1 day. Immediately after mixing cyclohexane and Na-SG-I, fine gas bubbles (H$_2$) are produced due to the reaction of Na-SG-I with moisture. After a few hours without stirring, bubbling stops. Upon standing without stirring, Na-SG-I settles down leading back to clear and colorless cyclohexane. Just prior using, cyclohexane was distilled off from Na-SG-I and transferred under dry atmosphere into the polymerization reactor.

Method C. Ordinary cyclohexane used straight from the commercial bottle with no purification.

Anionic styrene polymerization initiated by sec-BuLi was performed using cyclohexane purified according to the different above methods. In the three systems, the styrene monomer was purified over Bu$_2$Mg (Method A). After addition of sec-BuLi, the color of reaction media turned to orange, a characteristic of living polystyrene. Ethanol was added to terminate the reaction. Among the different tests performed, results from the most representative tests are shown in Table 1. These results show that when the targeted polymer molar mass is low (M$_n$=10,000), all the polymers exhibit the theoretically expected molar mass independently of the purification method (see Examples 1a, 1b, and 1c). However, for higher targeted molar mass (M$_n$=50,000), which corresponds to a five times lower concentration in active species, a significant deviation occurs for the non-dried solvent (see Example 1f). On the other hand, drying methods based on the use of sec-BuLi (see Example 1d) or Na-SG-I (see Example 1e) gives experimental molar masses in good agreement with theory. This is consistent with a negligible contribution of impurities in these two systems.

TABLE 1

Influence of drying conditions on the anionic polymerization Of styrene[a] initiated by sec-BuLi in cyclohexane at r.t.[b]

| Theoretical M$_n$ | Cyclohexane drying process | | |
|---|---|---|---|
| | PSLi[c] | Na-SG-I[d] | Bottle[e] |
| | Polymerization results | | |
| | Example 1a | Example 1b | Example 1c |
| M$_n$(calc'd) = 10,000 | M$_n$ = 8,000 M$_w$/M$_n$ = 1.07 | M$_n$ = 7,500 M$_w$/M$_n$ = 1.08 | M$_n$ = 7,300 M$_w$/M$_n$ = 1.08 |
| | Example 1d | Example 1e | Example 1f |
| M$_n$(calc'd) = 50,000 | M$_n$ = 50,000 M$_w$/M$_n$ = 1.02 | M$_n$ = 45,000 M$_w$/M$_n$ = 1.03 | M$_n$ = 74,000 M$_w$/M$_n$ = 1.09 |

[a]Dried over Bu$_2$Mg and vacuum distillated.
[b]Conversion ~100%.
[c]Dried over PSLi seeds and vacuum distillated.
[d]Dried with Na-SG-I (100 mg in 50 ml solvent) and vacuum distillated.
[e]From the bottle (no purification).

EXAMPLE 2

Tetrahydrofuran (THF)

Method A. THF (50 ml) was refluxed over CaH$_2$ for 3 hours. This was followed by subsequent distillation into a flask equipped with PTFE stopcocks containing sodium metal (~0.2 g) and benzophenone (~0.2 g). After a few second, the THF solution colored blue. After additional stirring for 1 day, the color of THF changed from blue to deep purple. The deep purple color due to dianion of sodium-benzophenone indicates that THF is completely dry. Then, following a distillation under inert atmosphere from sodium-benzophenone, THF is ready to be used for polymerization.

Method B. THF was purified in a similar way to cyclohexane (Method B). THF from the bottle (50 ml) was stirred in the presence of Na-SG-I (200 mg) for 2 days at room temperature and distilled under inert atmosphere into the polymerization reactor. As with cyclohexane, evolution of fine gas bubbles is observed during the THF drying procedure. During the stirring of the THF over the Na-SG-I, the solution turned brown. However, upon standing for one hour without stirring, the brown particles settled to the bottom of flask and the THF became clear and colorless.

Method C. Ordinary THF used straight from the commercial bottle with no purification.

A similar approach to Example 1 was followed for purification of THF, a typical solvent of anionic polymerization which may contain larger amounts of impurities than hydrocarbons. Because of the high reactivity of active species, the polymerization reactions must be conducted at very low temperatures (−80° C.). Even in these conditions, the polymerization reaction is very fast (usually, polymerization is completed within a few seconds). The THF and styrene were dried separately over Na-SG-I. After the addition of THF to the polymerization flask, sec-BuLi (0.182 mmol) was injected at −80° C. Finally, styrene (2.0 ml, 17.5 mmol) was injected and left to react for 20 min at −80° C. Termination of the polymerization and polymer recovery were performed (see Example 2b). Three different types of THF purification/drying process were compared and are listed above in the three methods.

Representative results are collected and shown in Table 2. In the absence of a drying process for the THF, the polystyrene product resulted in a much higher molar mass than predicted (see Example 2c). This suggests that about 90% of the active species have been deactivated prior to the polymerization initiation. The results obtained with the conventional drying agent (Na/benzophenone) (see Example 2a) and with the new Na-SG-I (see Example 2b) are very close to optimum, although not perfect. In both cases, about ⅓ of the sec-BuLi has been deactivated prior to polymerization. Nevertheless, the results show a clear and almost equivalent capacity of Na-SG-I to dry THF compared to the conventional Na/benzophenone with the Na-SG-I having a significantly smaller and better polydispersity. The results shown in Table 2 indicate that Na-SG-I is as effective as Na/benzophenone to dry THF for use in anionic polymerization.

TABLE 2

Influence of drying conditions on the anionic polymerization of styrene[a] initiated by sec-BuLi in THF at −80° C.[b]

| | THF Drying Process | | |
|---|---|---|---|
| | Na—Ph$_2$C=O[c] | Na-SG-I[d] | Bottle[e] |
| | Polymerization Results | | |
| Theoretical M$_n$ | Example 2a | Example 2b | Example 2c |
| M$_n$(calc'd) = 9,800 | M$_n$ = 15,000 | M$_n$ = 16,000 | M$_n$ = 83,000 |
| | M$_w$/M$_n$ = 1.16 | M$_w$/M$_n$ = 1.04 | M$_w$/M$_n$ = 1.15 |

[a]Dried over Bu$_2$Mg and vacuum distillated.
[b]Conversion ~100%.
[c]Drying over Na/benzophenone and vacuum distillated.
[d]Drying with Na-SG-I (500 mg in 120 ml solvent) and vacuum distillated.
[e]From the bottle (no purification).

Purification and Drying of Monomers with Polymerization Efficiency Measurements

To demonstrate the removal water and other impurities from liquid monomers, several exemplary monomers typically used in anionic polymerizations were contacted with Na-SG-I according to the invention.

EXAMPLE 3

Styrene

Method A. Styrene (125 ml) was distilled in a glass flask and it was kept at room temperature (20° C.) over di-n-butylmagnesium (Bu$_2$Mg, 1 M in heptanes, ~2 ml) for 1 hour. Then styrene was distilled from Bu$_2$Mg solution under vacuum conditions and used for the polymerization.

Method B. Styrene was purified in a similar way to cyclohexane Method B. Styrene (15 ml) was stirred in the presence of Na-SG-I (75 mg) for 1 day at room temperature and then distilled under vacuum and used for polymerization. Upon adding Na-SG-I to styrene, a light blue colors appears while fine bubbles are generated at the beginning. Bubbling stopped after a few minutes and the blue color disappeared on the following day. Even after keeping styrene with Na-SG-I longer than 1 week at room temperature, only a trace amount of polystyrene was formed (~1%). When a similar procedure was performed at 45° C., styrene polymerization was observed after 1 day, yielding high molar mass polystyrene.

Method C. Ordinary styrene used straight from the commercial bottle with no purification.

Including the three different drying and purification methods listed above, the cyclohexane solvent used in the polymerization was dried separately over Na-SG-I. Cyclohexane (15 mL) and styrene (2.0 ml, 17.5 mmol), dried separately in the presence of Na-SG-I and then distilled, were added into a 50 mL round-bottom flask equipped with PTFE stopcocks. A cyclohexane solution of sec-BuLi (0.037 mmol) was then injected into the flask using a dried syringe under argon. The polymerization was left for 12 hours at room temperature before termination using a small quantity of ethanol and the polymer was recovered by precipitation into a large amount of ethanol (see Example 3a).

Using styrene without any purification (see Example 3b), a polymer of high molar mass (M$_n$=170,000) was obtained. The theoretical calculated value (M$_n$=50,000) was much lower. This is consistent with the deactivation of approximately 70% of the polymerization initiator molecules. Between the classical drying and purification method (Example 1e) and the new Na-SG-I (see Example 3a) technique, no significant difference is observed. In both cases, the experiments succeeded in obtaining polystyrene with the predicted molar masses and narrow molar mass distributions, or polydispersity. It is known that commercially available styrene contains 4-tert-butylcatechol (10-15 ppm) as a polymerization inhibitor, which, in turn, reacts with the anionic active species to impede polymerization. It follows from the results shown in Table 3 that Na-SG-I is able to react with the water present in the styrene, but also with the other impurities within styrene allowing the preparation of styrene of excellent purity for polymerization. In conclusion, Na-SG-I showed approximately the same effectiveness for styrene drying and purification as the commercial procedure using Bu$_2$Mg.

TABLE 3

Influence of drying conditions on the anionic polymerization of styrene initiated by sec-BuLi in cyclohexane[a] at r.t.[b]

| | Styrene Drying Process | | |
|---|---|---|---|
| | Bu$_2$Mg[c] | Na-SG-I[d] | Bottle[e] |
| | Polymerization Results | | |
| Theoretical M$_n$ | Example 1e | Example 3a | Example 3b |
| M$_n$(calc'd) = 50,000 | M$_n$ = 45,000 | M$_n$ = 55,000 | M$_n$ = 170,000 |
| | M$_w$/M$_n$ = 1.03 | M$_w$/M$_n$ = 1.04 | M$_w$/M$_n$ = 1.65 |

[a]Dried over Na-SG-I (100 mg in 50 ml solvent) and vacuum distillated.
[b]Conversion ~100%.
[c]Dried over Bu$_2$Mg and vacuum distillated.
[d]Dried with Na-SG-I (75 mg in 15 ml styrene) and vacuum distillated.
[e]From the bottle (no purification).

EXAMPLE 4

Isoprene

Method A. Isoprene (125 ml) was stored over Bu$_2$Mg (1M in heptanes, ~2 ml) in a glass flask equipped with PTFE stopcocks at room temperature for 1 h and distilled under vacuum conditions.

Method B. Isoprene was purified in a similar way to cyclohexane Method A. Isoprene (15 ml) was stirred in the presence of Na-SG-I (120 mg). Almost the same behavior was observed as for styrene.

Method C. Ordinary isoprene used straight from the commercial bottle with no purification.

The procedure used here was similar to that discussed above for the polymerization of styrene in Example 3. The same technique as with styrene was used for the purification of isoprene. The cyclohexane used for the polymerization was dried with Na-SG-I prior to its use. At first, the target molar mass of the polyisoprene was set to be $M_n$=16,000. A good agreement was observed between theoretical and experimental molar masses both for isoprene dried over $Bu_2Mg$ and Na-SG-I. In the case of using isoprene without any purification, the experimental molar mass is about twice as high as the expected value (see Example 4c), indicating the deactivation of approximately 50% of the active species. With increasing theoretical molar mass to 32,000 g/mol, the non-purified from the bottle isoprene resulted in only low isoprene conversion with the production of polyisoprene of molar masses higher than 110,000 g/mol with broad molecular weight distributions (see Example 4f). This confirms that commercially available isoprene contains more impurities than styrene.

In contrast, anionic polymerization of isoprene dried with conventional $Bu_2Mg$ (see Examples 4a and 4d) or the new Na-SG-I method (see Examples 4b and 4e) proceeded quantitatively to give well-controlled polyisoprene with predicted molecular weights and narrow molecular weight distributions. Cyclohexane (15 ml) and isoprene (3.0 ml, 30.0 mmol) were dried separately over Na-SG-I and then distilled under dry atmosphere into a glass reactor. Isoprene polymerization was initiated by adding sec-BuLi (0.0638 mmol) and the reaction was left over night at room temperature before its termination and polymer precipitation into ethanol (see Example 4e). These results are shown in Table 4 and prove an incredibly efficient purification method for commercial isoprene using Na-SG-I.

TABLE 4

Influence of drying conditions on the anionic polymerization of isoprene initiated by sec-BuLi in cyclohexane[a] at r.t.[b]

| | Isoprene Drying Process | | |
|---|---|---|---|
| Theoretical $M_n$ | $Bu_2Mg$[c] | Na-SG-I[d] | Bottle[e] |
| | Polymerization Results | | |
| | Example 4a | Example 4b | Example 4c |
| $M_n$(calc'd) = 16,000 | $M_n$ = 17,000 $M_w/M_n$ = 1.04 | $M_n$ = 15,000 $M_w/M_n$ = 1.05 | $M_n$ = 30,000 $M_w/M_n$ = 1.10 |
| | Example 4d | Example 4e | Example 4f |
| $M_n$(calc'd) = 32,000 | $M_n$ = 31,000 $M_w/M_n$ = 1.06 | $M_n$ = 32,000 $M_w/M_n$ = 1.07 | $M_n$ = 110,000 $M_w/M_n$ = 1.37 Conv. < 10% |

[a]Dried over Na-SG-I (100 mg in 50 ml solvent) and vacuum distillated.
[b]Conversion ~100%.
[c]Dried over $Bu_2Mg$ and vacuum distillated.
[d]Dried with Na-SG-I (120 mg in 15 ml isoprene) and vacuum distillated.
[e]From the bottle (no purification).

Purification and Drying of Monomer/Solvent Mixtures with Polymerization Efficacy Measurements

EXAMPLE 5

Purification and Drying of both Cyclohexane and Styrene Followed by Polymerization with and without Distillation A mixture of cyclohexane (15 ml) and styrene (17.5 mmol) was stirred with Na-SG-I (100 mg) for 2 days at room temperature and then distilled from Na-SG-I under vacuum. The monomer and solvent mixture was then used for polymerization.

As already mentioned, the polymerization of styrene dried over the Na-SG-I and vacuum distilled proceeded to give well-controlled polystyrene (Example 3b). Almost same results are obtained, in the case of drying a mixture of styrene and cyclohexane over Na-SG-I followed by vacuum distillation and polymerization initiation by addition of sec-BuLi to the distillated mixture (see Example 5a).

To show another important advantage of using the Na-SG-I powders, actual polymerizations were performed in the presence of Na-SG-I without distillation. Cyclohexane was dried over Na-SG-I and dried and distilled styrene and sec-BuLi were directly added to the cyclohexane over Na-SG-I. 15 mL of cyclohexane was dried with Na-SG-I (100 mg). Styrene (2.0 ml, 17.5 mmol) which was purified over Na-SG-I and then distilled was added to the cyclohexane containing Na-SG-I. Styrene polymerization was initiated by adding sec-BuLi (0.037 mmol) to the mixture of cyclohexane, styrene, and Na-SG-I. The reaction was kept for 1 night at room temperature. This proves the ability to perform polymerizations in the presence of Na-SG-I product (see Example 5b). Ethanol was added to the reaction to quench the living polystyrene and also deactivate Na-SG-I as shown by the evolution of fine gas bubbles.

The agreement between theoretical and experimental polystyrene molar masses, as well as polydispersity, remains excellent, indicating that it is not necessary to remove Na-SG-I prior to the polymerization step. The Na-SG-I has the ability to act as an in situ drying agent, but not as an initiator for the styrene polymerization. Therefore, the use of Na-SG-I dramatically facilitates the anionic polymerization. This approach is of interest both for laboratory scale and for industrial applications of living anionic polymerization.

Attempts to dry a mixture of cyclohexane and styrene over the Na-SG-I without further distillation of the styrene were not as successful with only Na-SG-I (see Example 5c, exemplifying molar masses of about 80,000 g/mol, instead of 50,000 g/mol). The mixture of cyclohexane (15 ml) and styrene (17.5 mmol) in a glass flask equipped with PTFE stopcocks was stirred with Na-SG-I (100 mg) for 2 days at room temperature. The solvent+monomer+Na-SG-I mixture were directly used for polymerization without any distillation steps or filtration. This experiment was repeated and yielded similar results. It is suspected that the stabilizer (4-tert-butylcatechol) or other impurities present into styrene could not be completely neutralized by Na-SG-I without using significant excess of the Na-SG-I. The results are shown in Table 5.

TABLE 5

Anionic Polymerization of Styrene initiated by sec-BuLi
in Cyclohexane at Room Temperature (r.t.)[a]

| | Cyclohexane, Styrene Purification Methods | | | |
|---|---|---|---|---|
| | Na-SG-I[b),c)] | Na-SG-I[d)] | in situ Na-SG-I[e),c)] | in situ Na-SG-I[f)] |
| | Polymerization Results | | | |
| Theoritical $M_n$ | Example 3b | Example 5a | Example 5b | Example 5c |
| $M_n$(calc'd) = 50,000 | $M_n$ = 55,000 $M_w/M_n$ = 1.04 | $M_n$ = 58,000 $M_w/M_n$ = 1.04 | $M_n$ = 57,000 $M_w/M_n$ = 1.06 | $M_n$ = 80,000 $M_w/M_n$ = 1.30 |

[a)]Conversion ~100%.
[b)]Cyclohexane was dried with Na-SG-I (100 mg in 50 ml solvent) and vacuum distilled.
[c)]Styrene was dried with Na-SG-I (75 mg in 15 ml styrene) and vacuum distilled.
[d)]Mixture of styrene (2 ml) and cyclohexane (15 ml) was dried over Na-SG-I (100 mg) and vacuum distillated.
[e)]Na-SG-I 100 mg in-situ in cyclohexane (50 mL), Na-SG-I kept in the polymerization medium.
[f)]Mixture of styrene (2 ml) and cyclohexane (15 ml) was dried with Na-SG-I (165 mg), Na-SG-I kept in the polymerization medium.

Purification of styrene over Na-SG-I, according to the invention, followed by distillation is at least as effective as using dibutylmagnesium or trialkylaluminum. It is not only water, but also the stabilizer 4-tert-butylcatechol, which is likely converted into the corresponding phenolate that can be eliminated by this treatment followed by styrene distillation. When the distillation step is suppressed and polymerization is performed in situ, the phenolate salt, which is not totally inactive, may interact with the growing species, yielding partial deactivation.

EXAMPLE 6

Purification and Drying of both Cyclohexane and Isoprene Followed by Polymerization with and without Distillation The same process in Example 5 was used in order to investigate whether the distillation of the reactants and solvents after Na-SG-I drying was necessary or not. Three experiments performed under different types of isoprene and cyclohexane purification/drying methods were compared:

EXAMPLE 6A

Isoprene and Cyclohexane Dried Separately over Na-SG-I and then Vacuum Distillated

EXAMPLE 6B

A Mixture of Isoprene and Cyclohexane Dried over Na-SG-I and then Vacuum Distilled Before Addition of sec-BuLi

EXAMPLE 6C

A Mixture of Isoprene and Cyclohexane Dried over Na-SG-I and Used Directly for polymerization by Addition of sec-BuLi without Vacuum Distillation In all cases, as shown in Table 6, excellent agreement was observed between theoretical and experimental polyisoprene molar masses. Therefore, it can be seen that controlled polymerization of isoprene may proceed in the presence of Na-SG-I. Isoprene polymerization can thus be achieved easily by all of the components together, the solvent, the isoprene, and the Na-SG-I for a few hours at room temperature and adding directly butyl lithium to the mixture to get a living/controlled polymerization of the dienic monomer.

TABLE 6

Anionic Polymerization of Isoprene[a)]
initiated by sec-BuLi in Cyclohexane at r.t.[b)]

| | Cyclohexane, Isoprene Purification Methods | | |
|---|---|---|---|
| | Na-SG-I[c)] | Na-SG-I[d)] | in situ Na-SG-I[e)] |
| | Polymerization Results | | |
| Theoritical $M_n$ | Example 6a | Example 6b | Example 6c |
| $M_n$(calc'd) = 10,000 | $M_n$ = 11,000 $M_w/M_n$ = 1.05 | $M_n$ = 8,600 $M_w/M_n$ = 1.04 | $M_n$ = 12,000 $M_w/M_n$ = 1.04 |

[a)]Dried with Na-SG-I (120 mg in 15 ml isoprene) and vacuum distillated.
[b)]Conversion ~100%.
[c)]Dried with Na-SG-I (100 mg in 50 ml solvent) and vacuum distilled.
[d)]Mixture of isoprene (3.0 ml) and cyclohexane (15 ml) was dried with Na-SG-I (100 mg) and vacuum distillated.
[e)]Mixture of isoprene (3.0 ml) and cyclohexane (15 ml) was dried with Na-SG-I (110 mg), Na-SG-I kept in the polymerization medium.

Anionic polymerization of isoprene dried with Na-SG-I proceeded quantitatively to give well-controlled polyisoprene, which possess predicted molar weight and narrow distributions. These results are consistent with a strong efficiency to neutralize the impurities contained in commercial isoprene. In contrast to styrene, the mixture of isoprene and cyclohexane can be dried over minimal amounts of Na-SG-I and used for polymerization preparation directly in situ without the need for vacuum distillation. Agreement was observed between the theoretical and the experimental molar masses.

EXAMPLE 7

Drying of MethylMethacrylate (MMA)

After the mixing with methyl methacrylate (MMA, 10 ml) and Na-SG-I (80 mg) at room temperature for 1 night, a polymer of high molar mass ($M_n$=105,000) was obtained in about 25% yield. In the case of using Na-SG-II compound (MMA; 10 ml, Na-SG-II; 100 mg), no polymerization occurs after 24 hours. This shows that Na-SG-I possesses higher reactivity with MMA and is able to initiate its polymerization. On the contrary Na-SG-II does not initiate the polymerization and can be used as a drying agent.

EXAMPLE 8

Use Na-SG-II for the Purification/Drying of Cyclohexane and Styrene

Styrene and cyclohexane were dried separately over Na-SG-II and then vacuum distilled. Upon subsequent polymerization, good agreement was observed between theoretical and experimental molar masses (Mn(calcd)=50,000, Mn(obsd)=51,000).

Styrene which was purified with Na-SG-II and following distillation was added to cyclohexane over Na-SG-II. Observed molar mass (Mn(obsd)=67,000) is slightly higher than target molar mass (Mn(calcd)=50,000). This shows that Na-SG-II can be used as a drying system.

EXAMPLE 9

Purification by Passing the Solvent/Monomer through a SiGNa Column without Further Distillation To further enhance the utility of a Stage I Group I/porous metal oxide composition or a Stage II Group 1 metal/porous metal oxide composition. for anionic polymerization, a column packed with Na-SG-I was prepared and used for the drying/purification of cyclohexane and styrene.

Method A: Cyclohexane was passed through the Na-SG-I column during its transfer into the polymerization flask and styrene, previously dried over Na-SG-I in a separate flask, was then vacuum distillated into the polymerization flask. BuLi was added to start the polymerization.

Method B: Cyclohexane was passed through the Na-SG-I column, followed by styrene which was passed through the same Na-SG-I column or a mixture of cyclohexane and styrene were passed through the Na$_2$K-SG-I column and directly stored in the polymerization flask. BuLi was added to start the polymerization

TABLE 7

Anionic Polymerization of Styrene Initiated by sec-BuLi in cyclohexane at r.t.[a] Drying using a filled column

|  | Drying Method A | Drying Method B | Drying Method B |
|---|---|---|---|
| Cyclohexane | Na-SG-I column[b] | Na-SG-I column | Na$_2$K-SG-I column |
| Styrene | Na-SG-I and distillation[c] | Na-SG-I column | Na$_2$K-SG-I column |

| | Polymerization results | | |
|---|---|---|---|
|  | Example 9a | Example 9d | Example 9f[e] |
| Cycle 1 | $M_n$ = 51,000<br>$M_w/M_n$ = 1.07 | $M_n$ = 76,000<br>$M_w/M_n$ = 1.18 | $M_n$ = 40,000<br>$M_w/M_n$ = 1.08 |
|  | Example 9b[d] | Example 9e | Example 9g |
| Cycle 2 | $M_n$ = 40,000<br>$M_w/M_n$ = 1.07 | $M_n$ = 78,000<br>$M_w/M_n$ = 1.20 | $M_n$ = 37,000<br>$M_w/M_n$ = 1.10 |
|  | Example 9c |  | Example 9h[f] |
| Cycle 3 | $M_n$ = 47,000<br>$M_w/M_n$ = 1.13 |  | $M_n$ = 45,000<br>$M_w/M_n$ = 1.12 |

[a] Conversion ~100%. $M_n$(calcd) = 50,000.
[b] Purified by passing through the column packed with Na-SG-I.
[c] Dried with Na-SG-I (75 mg in 15 ml styrene) and vacuum distillated.
[d] $M_n$(calcd) = 38,000.
[e] $M_n$(calcd) = 47,000.
[f] $M_n$(calcd) = 45,000.

Using Method A, 3 successive polymerization reactions were performed using same column and reaction conditions. Polystyrene with controlled molecular weights (within the experimental error), and narrow molecular weight distributions were always achieved with quantitative yields. The Na-SG-I column works well to remove the impurity of cyclohexane and this column can be used in a repeated way.

Using Method B, two successive polymerization reactions were carried out. The two polymerizations (Examples 9d and 9e) proceeded quantitatively to produce polystyrenes but with significantly higher molecular weights ($M_n$=76,000-78,000) than expected molecular weight ($M_n$=50,000). This indicates a loss of active species due to the uncomplete purification of styrene. This is possibly the stabilizing agent since the experimental molecular weights values ($M_n$=76,000-78,000) are almost same as the in the case of in-situ polymerization (Example 3c; $M_n$=80,000 $M_w/M_n$=1.30). It is worthy to remind that in the case of using styrene without any purification (Example 3b), the resulting polymer has much higher molecular weight ($M_n$=170,000) and much broader molecular weight distributions ($M_w/M_n$=1.65).

These results indicate that Na-SG-I column shows a good effectiveness but do not yield quantitative styrene purification. However, controlled anionic styrene polymerization could be achieved by using Na$_2$K-SG-I column (Example 9f). It is also interesting to note that Na$_2$K-SG-I column also possess the capacity of repeatable use (3 cycles), even for styrene drying/purification.

These results suggest that a column of Na-SG-I for cyclohexane and a column of Na$_2$K-SG-I for cyclohexane and styrene can act as efficient drying agents and allow repeatable use without additional procedure. The advantage of this procedure is that there is no need to remove metal compounds from the resulting polymer (like in in situ drying according to the invention) and no need for subsequent distillation. These two advantages are of value both for laboratory scale and for industrial application of living anionic polymerizations. The solvent and/or monomer may be passed through the column as a liquid or distilled through the column to remove impurities according to a method of the invention. While the column used here was packed only with a Stage I Group 1 metal/porous metal oxide composition or a Stage II Group 1 metal/porous oxide composition, it is possible to mix the Stage I Group 1 metal/porous metal oxide compositions and Stage II Group 1 metal/porous oxide compositions themselves or with other common column material as long as the additional column material does not significantly impact the efficacy of the Stage I Group 1 metal/porous metal oxide compositions and Stage II Group 1 metal/porous oxide compositions. For example, it is possible to mix the Stage I Group 1 metal/porous metal oxide compositions and/or Stage II Group 1 metal/porous oxide compositions with additional porous metal oxides (e.g. silica or alumina), zeolite materials, activated carbon, diatomaceous earth, or other materials known in the art.

As shown by all of the above examples, Stage I Group 1 metal/porous oxide compositions or Stage II Group I metal/porous oxide compositions, such as Na-SG-I or Na-SG-II, can be used in almost identical conditions as other reported drying agents and impurity removers to prepare solvents for anionic polymerization, e.g. mixing Na-SG-I to the solvent followed by distillation under inert atmosphere of the solvent before use. Na-SG-I can be used in the very same way as a drying agent and impurity remover for olefinic monomers. Purification can be performed on bulk monomers at room temperature without any significant polymerization after several days. Monomers are thus recovered by distillation under inert atmosphere and are ready for anionic polymerization. The real advantage to this new process is that the solvent and monomer can be mixed and dried together over Stage I Group 1 metal/porous metal oxide compositions or a Stage II Group I metal/porous metal oxide compositions and this solvent/ monomer mixture recovered by distillation under inert atmosphere and directly used for polymerization. Being generally inertness of these compositions towards polymerization of styrenic and dienic monomers even allows polymerization to be performed in situ, i.e in the presence of the alkali metal/ porous oxide compositions. This can be achieved by adding directly the monomer, a Stage I Group 1 metal/porous metal oxide composition or a Stage II Group 1 metal/porous metal oxide composition, and the initiator (typically alkyllithium) into the system containing the solvent in order to initiate the anionic polymerization. In addition to their use in batches, it also becomes possible to dry solvent and monomer using a bed flow process or by passing them over a drying column containing a Stage I Group 1 metal/porous metal oxide composition or a Stage II Group 1 metal/porous metal oxide composition, the presence of residual drying agent in the polymerization media showing no effect on the anionic process.

According to the invention, Stage I Group 1 metal/porous metal oxide compositions, or Stage II Group 1 metal/porous metal oxide compositions, are useful to remove impurities and to dry solvents and monomers, e.g., styrenic and ethylenic monomers, used in anionic polymerizations. One important advantage of these compositions is their ability to purify, i.e. remove impurities and/or dry, simultaneously mixtures of the solvent and monomers, without inducing a significant polymerization of the latter. Another important characteristic is the capacity of the compositions to be totally inactive toward conventional anionic polymerization which allows them to be left in situ during the polymerization. Another important advantage of the invention is that Stage I Group 1 metal/porous metal oxide compositions, or Stage II Group 1 metal/porous metal oxide compositions preferably remaining in situ during the polymerization causes the distillation step in prior art process to be redundant. Furthermore, Stage I Group 1 metal/porous metal oxide compositions, or Stage II Group 1 metal/porous metal oxide compositions, used according to the invention, are useful as column packing materials for the drying/purification of the reagents of anionic polymerization. These two aspects represent important and significant progress facilitating the handling of anionic polymerization.

The claimed invention is:

1. A method for removing impurities from solvents or monomers, comprising the step of contacting a solvent, a liquid monomer, or a solvent-monomer mixture with a Stage I Group 1 metal/porous metal oxide composition or a Stage II Group 1 metal/porous metal oxide composition,
   wherein the porous metal oxide in the Stage II Group 1 metal/porous metal oxide composition contains silicon.

2. A method of claim 1, wherein the impurity is a protic impurity.

3. A method of claim 2, wherein the protic impurity is water.

4. A method of claim 1, wherein the impurity is a stabilizer or inhibitor.

5. A method of claim 1, further comprising, before the contacting step, the step of distilling the solvent or the liquid monomer.

6. A method of claim 1, wherein a drying agent is included in the solvent and the liquid monomer mixture.

7. A method of claim 1, further comprising, after the contacting step, the step of distilling the solvent or the liquid monomer.

8. A method of claim 1, wherein the contacting step comprises passing the solvent, the liquid monomer, or solvent-monomer mixture thereof through a column containing the Stage I Group 1 metal/porous metal oxide composition, the Stage II Group 1 metal/porous metal oxide composition, or a mixture thereof.

9. A method of claim 1, wherein the contacting step comprises distilling the solvent, the liquid monomer, or solvent-monomer mixture thereof through a column containing the Stage I Group 1 metal/porous metal oxide composition, the Stage II Group 1 metal/porous metal oxide composition, or a mixture thereof.

10. A method of claim 1, wherein the monomer is an olefinic monomer.

11. A method of claim 10, wherein the olefin monomer is a styrenic monomer, a dienic monomer, or a methacrylate monomer.

12. A method of claim 1, wherein the Stage I-Group 1 metal/porous metal oxide composition or the Stage II Group 1 metal/porous metal oxide composition contains an alkali metal or alkali metal alloy present in an amount ranging from about 35 to 40 wt. %.

13. A method of claim 1, wherein the porous metal oxide in the Stage II Group 1 metal/porous metal oxide composition is silica gel.

14. A method of claim 1, wherein the solvents or monomers are used in anionic polymerization.

15. An anionic polymerization process comprising the steps of:
   contacting a solvent, a liquid monomer, or a solvent-monomer mixture with a Stage I Group 1 metal/porous metal oxide composition or a Stage II Group 1 metal/porous metal oxide composition;
   optionally combining the liquid monomer and solvent, when the solvent or the monomer is separately contacted with the Stage I Group 1 metal/porous metal oxide composition or a Stage II Group 1 metal/porous metal oxide composition; and
   polymerizing the monomer under anionic polymerization conditions,
   wherein the porous metal oxide in the Stage II Group 1 metal/porous metal oxide composition contains silicon.

16. A method of claim 15, further comprising, after the contacting step, the step of distilling the solvent or the liquid monomer.

17. A method of claim 15, wherein the contacting step comprises passing the solvent, the liquid monomer, or solvent-monomer mixture thereof through a column containing the Stage I Group 1 metal/porous metal oxide composition or the Stage II Group 1 metal/porous metal oxide composition.

18. The anionic polymerization process of claim 15, wherein the Stage I Group 1 metal/porous metal oxide composition or the Stage II Group 1 metal/porous metal oxide composition contains an alkali metal or alkali metal alloy present in an amount ranging from about 35 to 40 wt. %.

19. A method of claim 15, wherein the polymerization is performed in situ by adding an initiator directly.

20. The anionic polymerization process of claim 15, wherein the porous metal oxide in the Stage II Group 1 metal/porous metal oxide composition is silica gel.

21. A method for removing impurities from a solvent, comprising the step of contacting a solvent with a Stage I Group 1 metal/porous metal oxide composition or a Stage II Group 1 metal/porous metal oxide composition, wherein the porous metal oxide in the Stage II Group 1 metal/porous metal oxide composition contains silicon, wherein the Stage I Group 1 metal/porous metal oxide composition or the Stage II Group 1 metal/porous metal oxide composition contains an alkali metal or alkali metal alloy present in an amount ranging from 35 to 40 wt. %.

22. A method for removing impurities from a solvent, comprising the step of contacting a solvent with a Stage I Group 1 metal/porous metal oxide composition or a Stage II Group 1 metal/porous metal oxide composition, wherein the porous metal oxide in the Stage II Group 1 metal/porous metal oxide composition contains silicon, wherein the porous metal oxide in the Stage II Group 1 metal/porous metal oxide composition is silica gel.

23. A method for removing impurities from a solvent, comprising the step of contacting a solvent with a Stage I Group 1 metal/porous metal oxide composition or a Stage II Group 1 metal/porous metal oxide composition, wherein the porous metal oxide in the Stage II Group 1 metal/porous metal oxide composition contains silicon, wherein the Group 1 metal is sodium or a sodium-potassium alloy and the porous metal oxide in the Stage I Group 1 metal/porous metal oxide composition or the Stage II Group 1 metal/porous metal oxide composition is silica gel.

* * * * *